US011529102B2

(12) United States Patent
Akl et al.

(10) Patent No.: US 11,529,102 B2
(45) Date of Patent: Dec. 20, 2022

(54) HEART SOUND NORMALIZATION

(71) Applicant: Analog Devices, Inc., Norwood, MA (US)

(72) Inventors: Tony J. Akl, Bedford, MA (US);
Venugopal Gopinathan, Boston, MA (US)

(73) Assignee: Analog Devices, Inc., Wilmington, MA (US)

( * ) Notice: Subject to any disclaimer, the term of this patent is extended or adjusted under 35 U.S.C. 154(b) by 399 days.

(21) Appl. No.: 16/699,998

(22) Filed: Dec. 2, 2019

(65) Prior Publication Data

US 2021/0161476 A1 Jun. 3, 2021

(51) Int. Cl.
| | |
|---|---|
| *A61B 5/00* | (2006.01) |
| *A61B 5/349* | (2021.01) |
| *A61B 5/0245* | (2006.01) |
| *A61B 7/04* | (2006.01) |
| *G06T 7/00* | (2017.01) |

(52) U.S. Cl.
CPC .......... *A61B 5/7235* (2013.01); *A61B 5/0006* (2013.01); *A61B 5/0245* (2013.01); *A61B 5/349* (2021.01); *A61B 7/045* (2013.01); *G06T 7/0012* (2013.01); *A61B 2562/02* (2013.01); *G06T 2207/30048* (2013.01)

(58) Field of Classification Search
CPC ....... A61B 5/7235; A61B 5/025; A61B 5/022; A61B 5/0225; A61B 5/0006; A61B 5/0245; A61B 5/349; A61B 7/045; A61B 2562/02; A61B 7/04; A61B 5/7257; G06T 7/0012; G06T 2207/30048; G10L 25/18; G10L 25/66
See application file for complete search history.

(56) References Cited

U.S. PATENT DOCUMENTS

| | | | |
|---|---|---|---|
| 6,869,404 | B2 | 3/2005 | Schulhauser et al. |
| 7,416,531 | B2 | 8/2008 | Mohler |
| 7,736,319 | B2 | 6/2010 | Patangay et al. |
| 7,780,606 | B2 | 8/2010 | Carlson et al. |
| 8,332,034 | B2 | 12/2012 | Patangay et al. |
| 8,597,197 | B2 | 12/2013 | Patangay et al. |
| 8,758,260 | B2 | 6/2014 | Zhang et al. |

(Continued)

FOREIGN PATENT DOCUMENTS

| | | |
|---|---|---|
| CN | 101291628 A | 10/2008 |
| CN | 202019342 U | 10/2011 |
| EP | 2143380 | 1/2010 |

OTHER PUBLICATIONS

Google Machine Translation of CN101291628A (see 16 above), 13 pages.

(Continued)

*Primary Examiner* — Scott M. Getzow
(74) *Attorney, Agent, or Firm* — Akona IP

(57) ABSTRACT

There is disclosed herein examples of systems and methods of processing captured heart sounds with frequency-dependent normalization. Based on an amount of attenuation of a first heart sound, a second heart sound can be normalized by modifying portions of the second heart sound by amounts determined based on frequencies of the portions. Accordingly, the systems and methods disclosed herein can result in different amounts of modification of different portions of the second heart sound based on the different frequencies of the portions.

18 Claims, 9 Drawing Sheets

(56) References Cited

U.S. PATENT DOCUMENTS

| | | |
|---|---|---|
| 8,827,919 B2 | 9/2014 | Siejko et al. |
| 9,622,664 B2 | 4/2017 | An et al. |
| 9,750,461 B1 | 9/2017 | Telfort |
| 2004/0127792 A1 | 7/2004 | Siejko et al. |
| 2005/0043643 A1 | 2/2005 | Priemer |
| 2007/0078491 A1 | 4/2007 | Siejko et al. |
| 2008/0013747 A1 | 1/2008 | Tran et al. |
| 2008/0015652 A1 | 1/2008 | Maile et al. |
| 2008/0039733 A1 | 2/2008 | Unver et al. |
| 2018/0214034 A1 | 8/2018 | Al Ahmad et al. |

OTHER PUBLICATIONS

Google Machine Translation of CN101291628A (see 17 above), 4 pages.

Debbal et al., *Frequency Analysis of the Heartbeat Sounds*, Biomedical Soft Computing and Human Sciences, vol. 13, No. 1, pp. 85-90 (2008), © 1995 Biomedical Fuzzy Systems Association, 7 pages.

EP Office Action issued in EP20207258.3 dated Mar. 30, 2021, 8 pages.

HEART SOUND NORMALIZATION

FIELD OF THE DISCLOSURE

This disclosure relates in general to the field of healthcare systems, and more particularly, though not exclusively, to a system and method for processing heart sounds.

BACKGROUND

In healthcare scenarios, heart sounds produced by a heart of a subject have been utilized in diagnosing health care issues of the subject. Historically, a care giver (such as a physician) would utilize a stethoscope to listen to the heart sounds of the subject and make inferences regarding the health status of the subject.

Legacy electronic healthcare systems have developed to capture the heart sounds of the subject in place of the care giver. In particular, the legacy electronic healthcare systems can capture the heart sounds and store representations of the heart sounds. In some of these legacy electronic healthcare systems, a sound sensor may be placed on the subject to capture the sounds.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

SUMMARY OF THE DISCLOSURE

Figure 1:
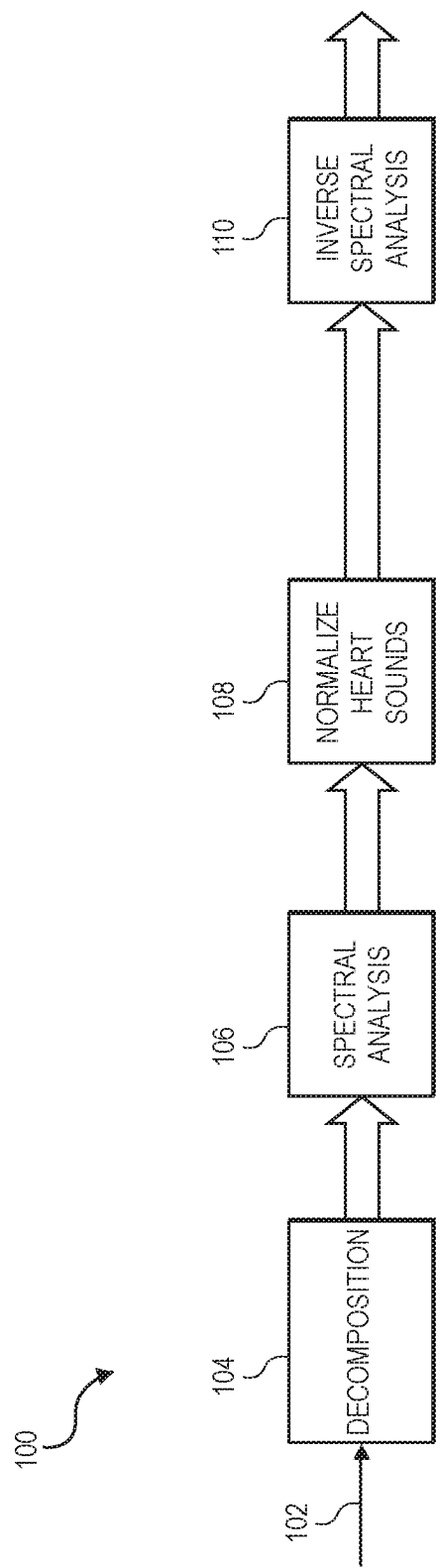
FIG. 1 illustrates an example procedure for processing heart sounds, according to embodiments herein.

There is disclosed herein examples of systems and methods of processing captured heart sounds with frequency-dependent normalization. Based on an amount of attenuation of a first heart sound, a second heart sound can be normalized by modifying portions of the second heart sound by amounts determined based on frequencies of the portions. Accordingly, the systems and methods disclosed herein can result in different amounts of modification of different portions of the second heart sound based on the different frequencies of the portions.

In certain embodiments, one or more computer-readable media having instructions stored thereon, wherein the instructions, in response to execution by a device, cause the device to determine an amount of attenuation between a capture of a first heart sound and a control for the first heart sound, the capture of the first heart sound captured during a test cycle, modify a first portion of a capture of a second heart sound by a first amount, wherein the capture of the second heart sound is captured during the test cycle, wherein the first portion corresponds to a first frequency range, and wherein the first amount is determined based on the amount of attenuation, and modify a second portion of the capture of the second heart sound by a second amount, wherein the second portion corresponds to a second frequency range, and wherein the second amount is determined based on the amount of the attenuation are disclosed herein.

In certain embodiments, a device for capturing heart sounds of a subject, comprising one or more sound sensors to sense heart sounds of the subject, and generate an electrical representation of the heart sounds is disclosed herein. Further in these embodiments, the device comprises one or more processors to identify a capture of a first heart sound from the electrical representation, compare the capture of the first heart sound with a control for the first heart sound to determine an amount of attenuation between the capture of the first heart sound and the control for the first heart sound, determine a first amount of modification and a second amount of modification based on the amount of attenuation, identify a capture of a second heart sound from the electrical representation, modify a first portion of the capture of the second heart sound by the first amount of modification, wherein the first portion of the capture corresponds to a first frequency range, and modify a second portion of the capture of the second heart sound by the second amount of modification, wherein the second portion of the capture corresponds to a second frequency range is disclosed herein.

In certain embodiments, a method of normalizing heart sounds, comprising comparing a capture of a first heart sound of a test cycle with a control for the first heart sound, determining an amount of attenuation between the capture of the first heart sound and the control for the first heart sound based on the comparison of the capture of the first heart sound and the control for the first heart sound, modifying a first portion of a capture of a second heart sound of the test cycle by a first amount, wherein the first portion corresponds to a first frequency range, and wherein the first amount is determined based on the amount of attenuation, and modifying a second portion of the capture of the second heart sound of the test cycle by a second amount, wherein the second portion corresponds to a second frequency range, and wherein the second amount is determined based on the amount of attenuation.

DETAILED DESCRIPTION

The following disclosure provides many different embodiments, or examples, for implementing different features of the present disclosure. Specific examples of components and arrangements are described below to simplify the present disclosure. These are, of course, merely examples and are not intended to be limiting. Further, the present disclosure may repeat reference numerals and/or letters in the various examples, or in some cases across different figures. This repetition is for the purpose of simplicity and clarity and does not in itself dictate a specific relationship between the various embodiments and/or configurations discussed. Different embodiments may have different advantages, and no particular advantage is necessarily required of any embodiment.

Disclosed herein are systems and methods for processing heart sounds with frequency-dependent normalization. Healthcare systems that capture heart sounds often utilize one or more sound sensors placed on the skin of a subject. However, placement of the sound sensors can result in attenuation of the heart sounds captured by the healthcare systems, often inadvertently. For example, improper placement of the sound sensors and/or the sound sensors being improperly attached to the skin of the subject can result in attenuation of the heart sounds. Further, the different portions of the heart sounds can be attenuated by different amounts based on the frequency of the different portions of the heart sounds. Failing to consider the attenuation of the heart sounds and the different amounts of attenuation of the different portions of the heart sounds based on the different frequencies can result in improper representations of the heart sounds and/or processing of improper representations of the heart sounds.

The systems and the methods disclosed herein can take into consideration the attenuation of the heart sound and the different amounts of attenuation of the different portions of the heart sounds based on the different frequencies. In particular, the systems and methods disclosed herein can compare a capture of a first heart sound with a control for the first heart sound to determine an amount of attenuation between the capture of the first heart sound and the control for the first heart sound, where the first heart sound should have a uniform amplitude across measurements. Each measurement may include one or more cardiac cycles. The systems and methods can utilize the amount of attenuation to modify captures of other heart sounds, where different portions of the other heart sounds may be modified by different amounts based on the different frequencies of the different portions.

FIG. 1 illustrates an example procedure 100 for processing heart sounds, according to embodiments herein. In particular, the procedure 100 may include normalization of one or more captures of heart sounds of a subject with a frequency-based approach.

The procedure 100 may initiate by receiving a representation of one or more cardiac cycles as input 102. For example, the input 102 may comprise an electrical signal that represents heart sounds included in the cardiac cycles. The electrical signal may be produced by a sound sensor that senses the heart sounds produced by the cardiac cycles and generates the electrical signal that represents the heart sounds. For example, the amplitude of the electrical signal can indicate an amplitude of the sound. Further, the electrical signal may be a time-domain representation of the heart sounds, where the electrical signal indicates the amplitude of the heart sounds over time.

Figure 2:
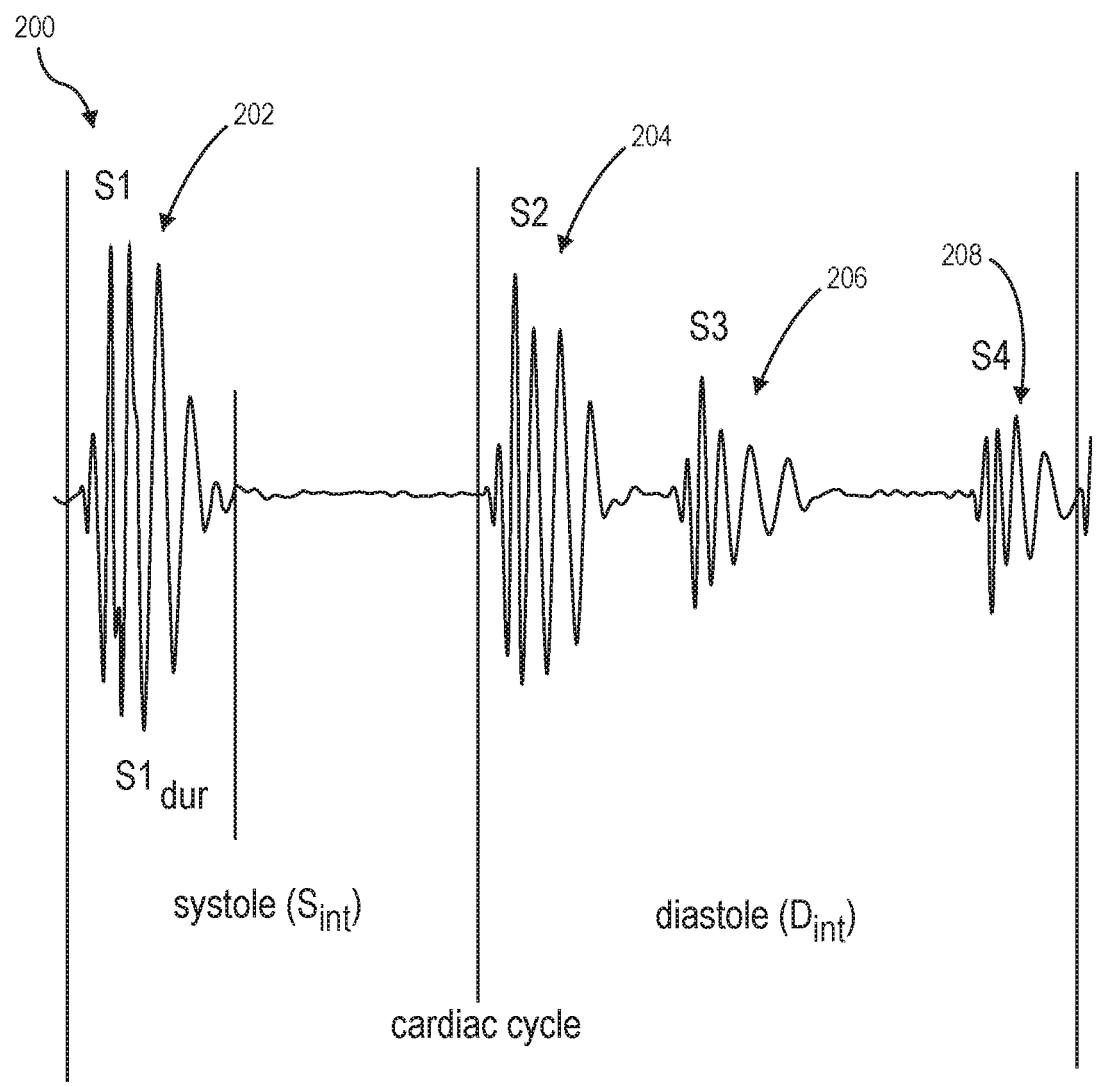
FIG. 2 illustrates an example electrical signal that may be received as the input of the procedure of FIG. 1, according to embodiments herein.

FIG. 2 illustrates an example electrical signal 200 that may be received as the input 102 of the procedure 100, according to embodiments herein. In particular, the electrical signal 200 illustrates a single cardiac cycle captured from the subject. A cardiac cycle includes a single heartbeat and the electrical signal 200 illustrates the heart sounds produced by a heart of the subject during the single heartbeat. The single heartbeat produces an S1 heart sound, an S2 heart sound, an S3 heart sound, and an S4 heart sound in the illustrated instance. In other instances, the S3 heart sound and/or the S4 heart sound may be omitted from the heart sounds produced by the heart of the subject during the heartbeat. While a single cardiac cycle is shown in the illustrated instance, it should be understood that in other instances multiple cardiac cycles may be received as the input 102 of the procedure 100. The cardiac cycle and/or the multiple cardiac cycles may be captured during a test cycle of a heart sound capture system.

The procedure 100 may include performing decomposition of the electrical signal in 104. The decomposition of the electrical signal may include identifying the different heart sounds from the electrical signal. In particular, the S1 heart sound, the S2 heart sound, the S3 heart sound, and/or the S4 heart sound represented by the electrical signal may be identified. Each of the heart sounds may be identified based on the amplitude of the heart sounds represented by the electrical signal, the frequency of the heart sounds represented by the electrical signal, the duration of the heart sounds represented by the electrical signal, the order of the heart sounds represented by the electrical signal, or some combination thereof.

FIG. 2 illustrates the heart sounds as identified within the procedure 100, according to embodiments herein. For example, the electrical signal 200 may include representations of one or more heart sounds that occur discrete in time. A cardiac cycle can include an S1 heart sound, an S2 heart sound, an S3 heart sound, an S4 heart sound, or some combination thereof. In the illustrated instance, the electrical signal 200 includes representations of an S1 heart sound 202, an S2 heart sound 204, an S3 heart sound 206, and an S4 heart sound 208. In the decomposition of the electrical signal 200, the S1 heart sound 202, the S2 heart sound 204, the S3 heart sound 206, and the S4 heart sound 208 can be identified, as indicated by the labeling of the heart sounds in FIG. 2. In other instances, representations of the S3 heart sound 206 and/or the S4 heart sound 208 may be omitted, such as when a heartbeat of the subject does not produce the S3 heart sound 206 and/or the S4 heart sound 208 (which can be a normal occurrence for a subject). In these instances, any combination of the S1 heart sound 202, the S2 heart sound 204, the S3 heart sound 206, and/or the S4 heart sound 208 can be identified while the heart sounds omitted from the electrical signal 200 may not be identified.

In some embodiments, the electrical signal 200 can be divided into different parts for processing during the decomposition of the electrical signal. In particular, the electrical signal 200 may be divided into different parts, where each part corresponds to a corresponding, identified heart sound. For example, a first part can include the S1 heart sound 202, a second part can include the S2 heart sound 204, a third part can include the S3 heart sound 206, and a fourth part can include the S4 heart sound 208 in the illustrated instance. In other embodiments, the electrical signal 200 can be divided into different parts at a later point during the procedure 100.

The procedure 100 may further include performing a spectral analysis of the electrical signal in 106. In particular, spectral analysis may be performed for each of the heart sounds identified in the decomposition of the electrical signal performed in 104. The spectral analysis can include converting the representations of the heart sounds into frequency-domain representations of the heart sounds. The representations of the heart sounds can be converted into frequency-domain representations by applying a Fourier transform to each of the representations of the heart sounds. For example, a Fourier transform applied to each of the representations can comprise a fast Fourier transform, a discrete Fourier transform, a continuous Fourier transform, or some combination thereof. For example, the S1 heart sound 202, the S2 heart sound 204, the S3 heart sound 206, and the S4 heart sound 208 can be converted into frequency-domain representations of each in the illustrated instance. The different parts of the electrical signal 200 corresponding to the different heart sounds can be converted separately.

Figure 3:
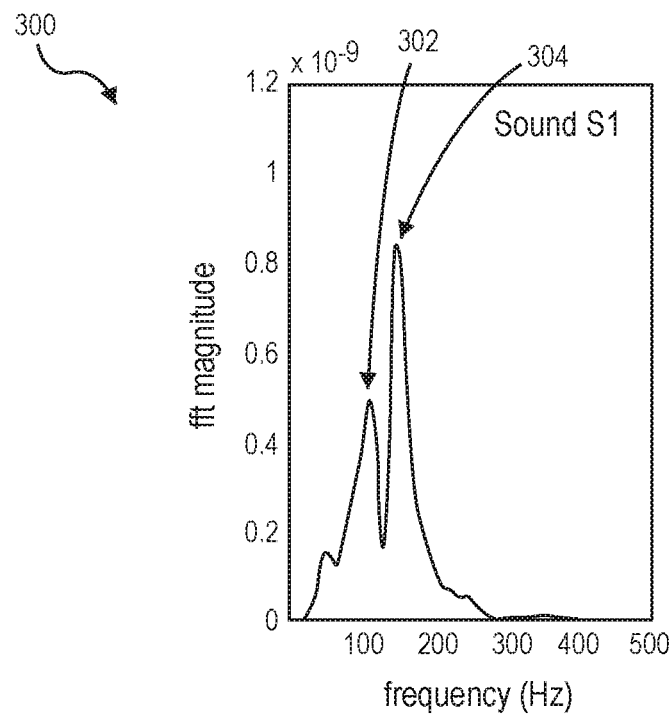
FIG. 3 illustrates an example frequency-domain representation of an S1 heart sound, according to embodiments herein.

FIG. 3 illustrates an example frequency-domain representation 300 of an S1 heart sound, according to embodiments herein. For example, the frequency-domain representation 300 may be a frequency-domain representation of the S1 heart sound 202. The frequency-domain representation 300 may be produced by performing the spectral analysis in 106 on part of the electrical signal 200 corresponding to the S1 heart sound 202. As can be seen, the frequency-domain representation 300 shows the amplitude of different portions of the S1 heart sound 202 corresponding to different frequencies. For example, the frequency-domain representation 300 shows a first peak 302 at a first frequency and a second peak 304 at a second frequency. In other embodiments, peaks may occur at different frequencies and/or may have different amplitudes in the frequency-domain representation 300.

Figure 4:
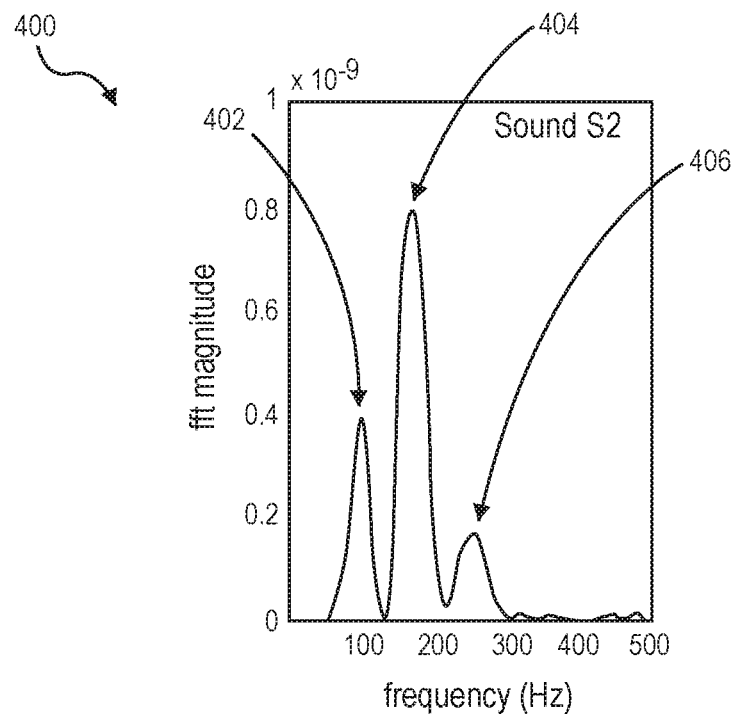
FIG. 4 illustrates an example frequency-domain representation of an S2 heart sound, according to embodiments herein.

FIG. 4 illustrates an example frequency-domain representation 400 of an S2 heart sound, according to embodiments herein. For example, the frequency-domain representation 400 may be a frequency-domain representation of the S2 heart sound 204. The frequency-domain representation 400 may be produced by performing the spectral analysis in 106 on part of the electrical signal 200 corresponding to the S2 heart sound 204. As can be seen, the frequency-domain representation 400 shows the amplitude of different portions of the S2 heart sound 204 corresponding to different frequencies. For example, the frequency-domain representation 400 shows a first peak 402 at a first frequency, a second peak 404 at a second frequency, and a third peak 406 at a third frequency. In other embodiments, peaks may occur at different frequencies and/or may have different amplitudes in the frequency-domain representation 400.

Figure 5:
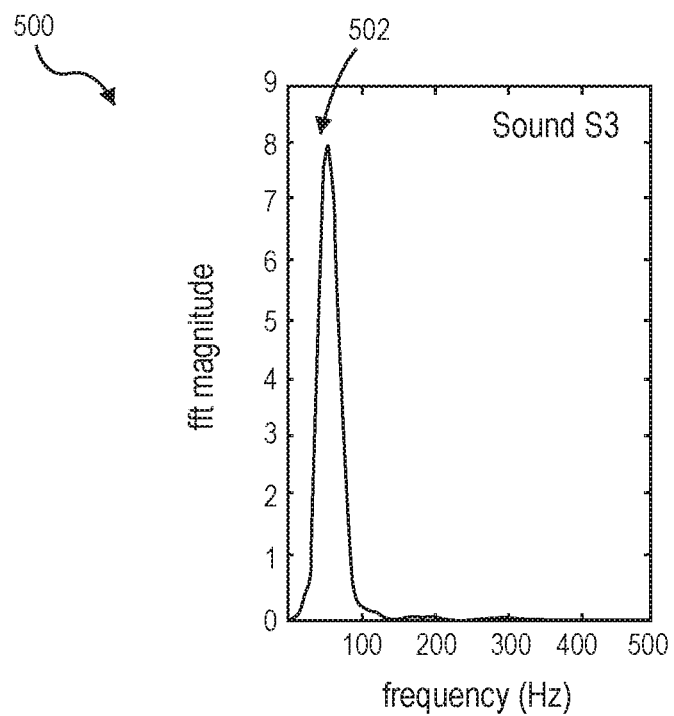
FIG. 5 illustrates an example frequency-domain representation of an S3 heart sound, according to embodiments herein.

FIG. 5 illustrates an example frequency-domain representation 500 of an S3 heart sound, according to embodiments herein. For example, the frequency-domain representation 500 may be a frequency-domain representation of the S3 heart sound 206. The frequency-domain representation 500 may be produced by performing the spectral analysis in 106 on part of the electrical signal 200 corresponding to the S3 heart sound 206. As can be seen, the frequency-domain representation 500 shows the amplitude of different portions of the S3 heart sound 206 corresponding to different frequencies. For example, the frequency-domain representation 500 shows a peak 502 at a frequency. In other embodiments, peaks may occur at different frequencies and/or may have different amplitudes in the frequency-domain representation 500.

Figure 6:
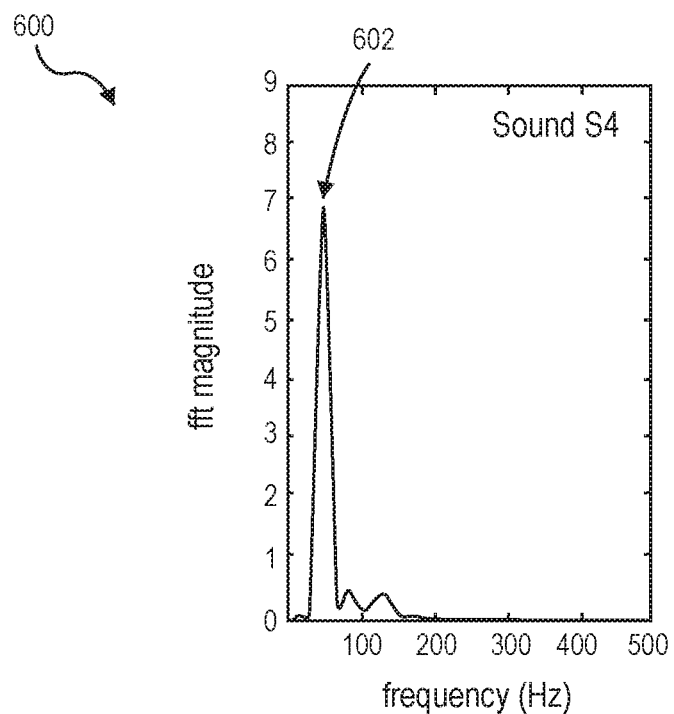
FIG. 6 illustrates an example frequency-domain representation of an S4 heart sound, according to embodiments herein.

FIG. 6 illustrates an example frequency-domain representation 600 of an S4 heart sound, according to embodiments herein. For example, the frequency-domain representation 600 may be a frequency-domain representation of the S4 heart sound 208. The frequency-domain representation 600 may be produced by performing the spectral analysis in 106 on part of the electrical signal 200 corresponding to the S4 heart sound 208. As can be seen, the frequency-domain representation 600 shows the amplitude of different portions of the S4 heart sound 208 corresponding to different frequencies. For example, the frequency-domain representation 600 shows a peak 602 at a frequency. In other embodiments, peaks may occur at different frequencies and/or may have different amplitudes in the frequency-domain representation 600.

The procedure 100 may further include normalizing the heart sounds in 108. Normalizing the heart sounds can include determining an amount of attenuation of one of the heart sounds and utilizing the amount of attenuation to modify one or more of the heart sounds. In other embodiments, normalizing the heart sounds can include determining amounts of attenuation of a portion of the heart sounds and utilizing the amounts of attenuation to modify one or more of the heart sounds. The modification of the one or more heart sounds may comprise amplifying the one or more heart sounds, attenuating the one or more heart sounds, or amplifying a portion of the one or more heart sounds and attenuating another portion of the one or more heart sounds. The amounts of attenuation may be caused by improper application of sound sensors (such as incorrect positioning of the sound sensors and/or the sound sensors not be placed air-tight against the skin of the subject), and/or other forms of imperfections that can cause audio coupling imperfections between a body of a subject and a sensor used to measure heart sounds in some instances.

The heart sound or heart sounds utilized for determining the amount of attenuation may be predefined or may be indicated by a user. For example, one or more captures of the S1 heart sound or one or more captures of the S2 heart sound may be utilized for determining the amount of attenuation or the amounts of attenuation in some embodiments, where amplitudes of the S1 heart sound and the S2 heart sound could be uniform across multiple cardiac cycles in most instances. In some embodiments, a user may be presented with a choice between utilizing one or more captures of the S1 heart sound or one or more captures of the S2 heart sound and may indicate which of the captures of the S1 heart sound or the captures of the S2 heart sound.

In some embodiments, the heart sound or heart sounds utilized for determining the amount of attenuation may be selected based on the heart sound or heart sound utilized for determining the amount of attenuation being expected to be negatively correlated with the heart sound or heart sounds to be modified. For example, the heart sound or heart sounds utilized for determining the amount of attenuation may be expected to remain constant while the heart sound or heart sounds to be modified may change, or the heart sound or heart sounds utilized for determining the amount of attenuation may be expected to change in a direction opposite to the direction of the heart sound or heart sounds to be modified may be expected to change in instances where the heart sound or heart sounds to be modified change. Selecting the heart sound or heart sounds to be negatively correlated with the heart sound or heart sounds to be modified may allow for a coupling factor to be eliminated and the heart sound or hearts to be modified without displaying coupling effects. The captures of the S1 heart sound, the S2 heart sound, the S3 heart sound, and/or the S4 heart sound can be modified based on the determined amount of attenuation or the amounts of attenuation.

Figure 7:
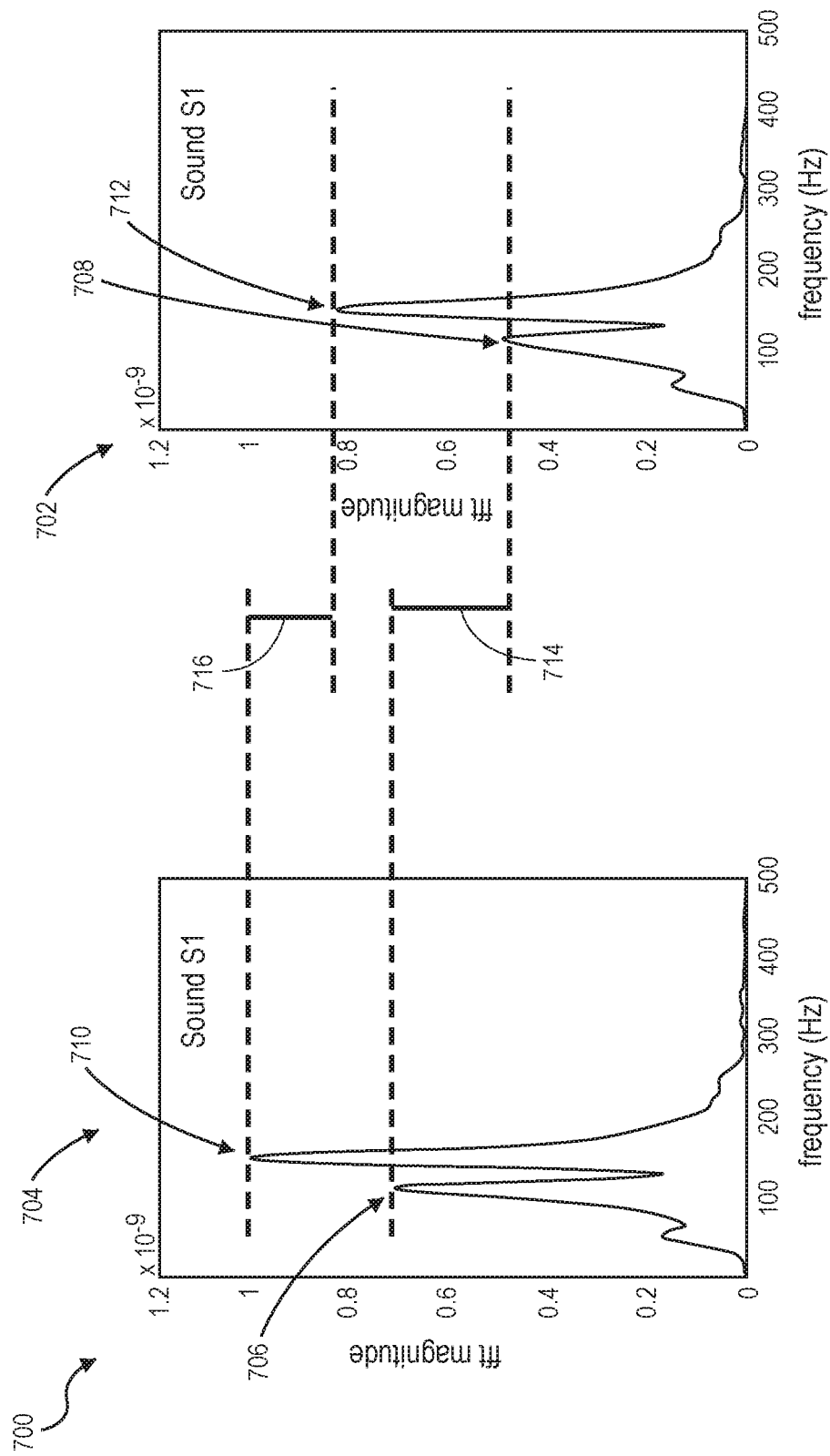
FIG. 7 illustrates an example procedure for determining an amount of attenuation, according to embodiments herein.

FIG. 7 illustrates an example procedure 700 for determining an amount of attenuation, according to embodiments herein. The procedure 700 may be performed as part of normalizing heart sounds in 108 (FIG. 1). The procedure 700 may include comparing a capture 702 of an S1 heart sound with a control 704 for the S1 heart sound to determine an amount of attenuation. In particular, a frequency-domain representation of the capture 702 of the S1 heart sound can be compared with the control 704 for the S1 heart sound to determine the amount of attenuation. In the illustrated instance, the S1 heart sound may be the predetermined heart sound for determining the amount of attenuation or an indication that the S1 heart sound should be utilized for determining the amount of attenuation. In other instances, other heart sounds may be the predetermined heart sound or an indication that the other heart sounds should be utilized for determining the amount of attenuation, such as the S2 heart sound may be utilized in other instances.

The capture 702 of the S1 heart sound may have been produced via the decomposition in 104 and the spectral analysis in 106. The capture 702 of the S1 heart sound may have been extracted from the electrical signal 200 (FIG. 2). In particular, the capture 702 of the S1 heart sound may be the frequency-domain representation 300 (FIG. 3) of the S1 heart sound in the illustrated instance.

The control 704 may be another frequency-domain representation of an S1 heart sound. The control 704 may have been captured during an initialization cycle, may have been captured during a previous test cycle, or may be generated by averaging multiple captures captured during an initialization cycle and/or previous test cycles. The control 704 may be captured in the presence of an authorized user (such as a health care provider) to assure that the frequency-domain representation is properly captured by a heart sound capture system. In some embodiments, controls may be captured for other heart sounds during the initialization cycle, may have been captured during the previous test cycle, or may be generated by averaging multiple captures captured during the initialization cycle and/or the previous test cycles. For example, controls may be captured for an S2 heart sound, an S3 heart sound, and/or an S4 heart sound in addition to the control for the S1 heart sound. The controls for the other heart sounds may be generated utilizing the heart sounds from the same cardiac cycle or cardiac cycles that were utilized for generating the S1 heart sound.

The procedure 700 may include comparing the capture 702 of the S1 heart sound to the control 704 for the S1 heart sound to determine an amount of attenuation. For example, one or more peaks, an average amplitude, a root mean square value, or other measurement of amplitude of the control 704 for the S1 heart sound can be compared with the corresponding measurement of the capture 702 of the S1 heart sound. In the illustrated instance, a first peak 706 of the control 704 occurring at a first frequency is compared with a first peak 708 of the capture 702 occurring at the first frequency to determine an amount of attenuation 714 at the first frequency. Further, a second peak 710 of the control 704 occurring at a second frequency is compared with a second peak 712 of the capture 702 occurring at the second frequency to determine an amount of attenuation 716 at the second frequency. As can be seen, the amount of attenuation 714 at the first frequency is greater than the amount of attenuation 716 at the second frequency, where the first frequency is lower than the second frequency. In other embodiments, one or more amounts of attenuation may be determined in the procedure 700 where each amount of attenuation can correspond to a corresponding frequency range. The determined amount or amounts of attenuation can be utilized for determining frequency-dependent amounts of modification for modifying the captures of heart sounds. In the illustrated instance, the capture 702 of the S1 heart sound is attenuated as compared to the control 704 to define the amount of attenuation 714. In other instances, the control 704 may be attenuated as compared to the capture 702 of the S1 heart sound to define the amount of attenuation 714.

Figure 8:
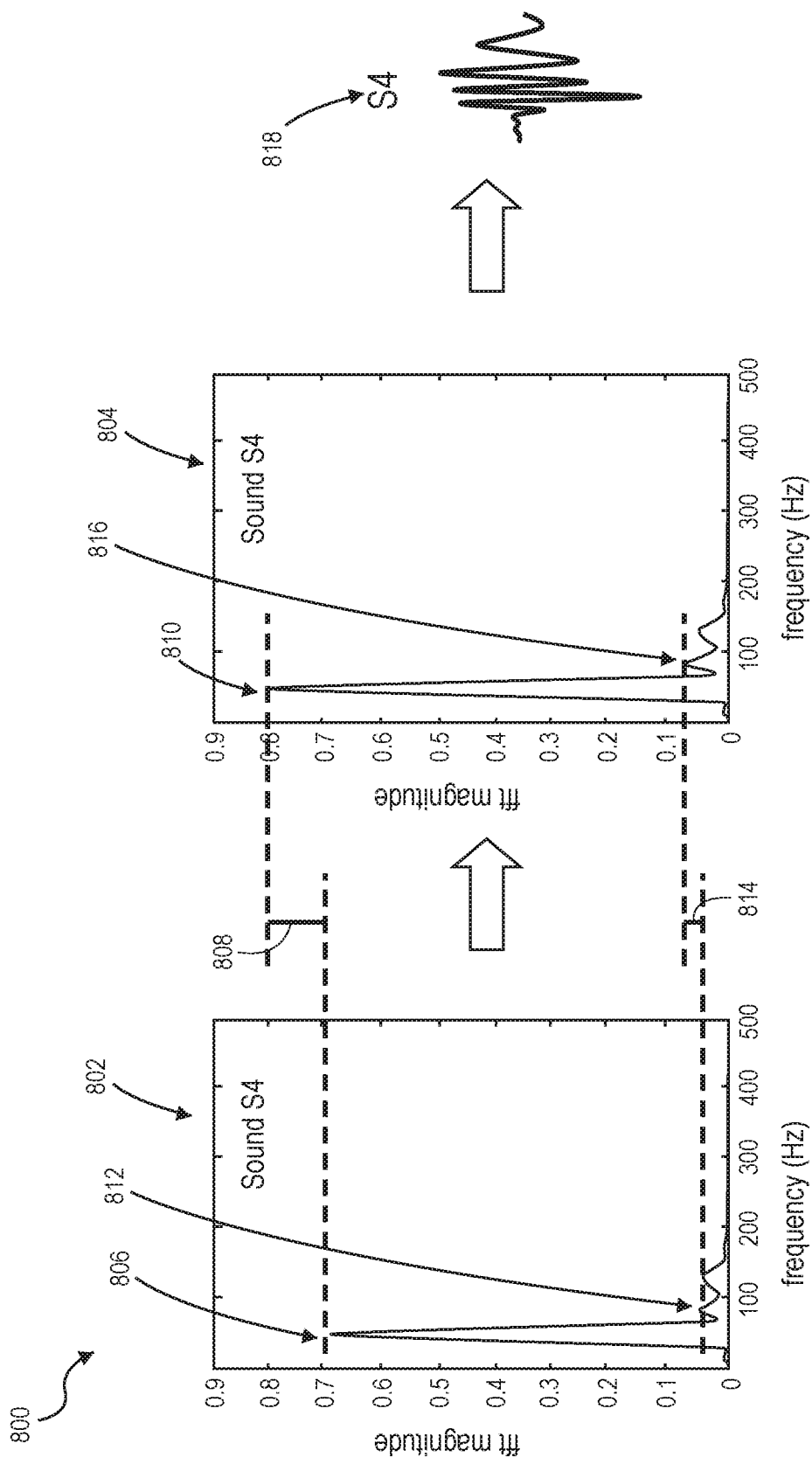
FIG. 8 illustrates an example procedure for modifying a capture of a heart sound, according to embodiments herein.

FIG. 8 illustrates an example procedure 800 for modifying a capture of a heart sound, according to embodiments herein. A portion of the procedure 800 may be performed as part of the normalizing of the heart sounds in 108. The procedure 800 may include modifying a capture 802 of an S4 heart sound to produce a normalized representation 804 of the S4 heart sound. In particular, a frequency-domain representation of the capture 802 of the S4 heart sound can be amplified to produce the normalized representation 804 of the S4 heart sound in the illustrated instance. In other instances, the frequency-domain representation of the capture 802 of the S4 heart sound can be attenuated to produce the normalized representation 804 of the S4 heart sound.

The capture 802 of the S4 heart sound may have been produced via the decomposition in 104 and the spectral analysis in 106. The capture 802 of the S4 heart sound may have been extracted from the electrical signal 200 (FIG. 2). In particular, the capture 802 of the S4 heart sound may be the frequency-domain representation 600 (FIG. 6) of the S4 heart sound in the illustrated instance. While the modification of the capture 802 of the heart sound is illustrated in the instance, it should be understood that illustrated instance is merely an example and the modification procedure described can be applied to other captures and other heart sounds.

The capture 802 of the S4 heart sound may be modified to produce the normalized representation 804 of the S4 heart sound. The amount of modification of the capture 802 of the S4 heart sound to produce the normalized representation 804 of the S4 heart sound may be determined based on the amount of attenuation of another heart sound. For example, the amount of modification can be determined based on the determined amounts of attenuation between the capture 702 (FIG. 7) of the S1 heart sound and the control 704 (FIG. 7) for the S1 heart sound. Further, whether the modification is amplification of the capture 802 or an attenuation of the capture 802 may be determined based on whether the capture 702 is attenuated as compared to the control 704 or the control 704 is attenuated as compared to the capture 702. For example, if the control 704 was captured in a state that resulted in an attenuated signal and if the source of attenuation is reduced or is no longer present when the capture 702 was made, the modification would be an attenuation of the capture 802 to maintain a consistent trend. Similarly, if the control 704 was captured in a state with no attenuation and if the source of attenuation is increased when the capture 702 was made, the modification would be an amplification of the capture 802 to maintain a consistent trend.

The amount of modification can be frequency-dependent where the amount of modification changes based on the different frequencies within the capture 802 of the S4 heart sound. In some embodiments, an equation can be applied to the amounts of attenuation to determine the amount of modification for each of the frequencies within the capture 802 of the S4 heart sound. In other embodiments, amounts of attenuation can be determined in procedure 700 (FIG. 7) for each of the frequencies within the capture 802 of the S4 heart sound, where the amounts of modification can be utilized for determining the amount of modification for each of the corresponding frequencies.

As can be seen, a first peak 806 of the capture 802 is modified by a first amount of modification 808 to produce a first peak 810 of the normalized representation 804. Further, a second peak 812 of the capture 802 is modified by a second amount of modification 814 to produce a second peak 816 of the normalized representation 804. The first amount of modification 808 and the second amount of modification 814 may have been determined based on the amount of attenuation 716 (FIG. 7) and the amount of attenuation 714 (FIG. 7) in the illustrated instance. The first amount of modification 808 can be greater than the second amount of modification 814 based on the difference in frequency being modified. In particular, the first amount of modification 808 may be greater than the second amount of modification 814 based on the first amount of modification 808 modifying a first frequency that is lower than a second frequency being modified by the second amount of modification 814. The amounts of modification being applied to the capture 802 can have particular amounts of modification for each frequency range, where each of the frequency ranges can include a single frequency or a range of frequencies.

The procedure 700 may include performing inverse spectral analysis in 710. In particular, inverse spectral analysis may be performed on the normalized representations of the heart sounds produced by the normalization of the heart sounds in 108. The inverse spectral analysis may include performing an inverse Fourier transform on the normalized representations of the heart sounds. The inverse spectral analysis may produce time-domain representations of the normalized representations of the heart sounds. The time-domain representations may be representations of the heart sounds without attenuation of the heart sounds that can cause improper analysis of the heart sounds. Accordingly, the time-domain representations generated with the normalized representations of the heart sounds can be utilized for analysis of the subject's heart sounds without concerns that the attenuation of the heart sounds could cause improper results of the analysis of the heart sounds.

FIG. 8 further illustrates an example of the performance of inverse spectral analysis in 710. In particular, the normalized representation 804 of the S4 heart sound is shown with inverse spectral analysis performed to produce a time-domain representation 818 of the S4 heart sound. The time-domain representation 818 may be produced by applying an inverse Fourier transform to the normalized representation 804 of the S4 heart sound. The time-domain representation 818 of the S4 heart sound may be utilized for analysis of the captured S4 heart sound without concerns that attenuation that may be caused by the sound sensors being improperly applied. While inverse spectral analysis is illustrated being performed on a capture of an S4 heart sound, it should be understood that that the inverse spectral analysis may be performed on captures of any heart sounds, include S1 heart sounds, S2 heart sounds, S3 heart sounds, and S4 heart sounds.

Figure 9:
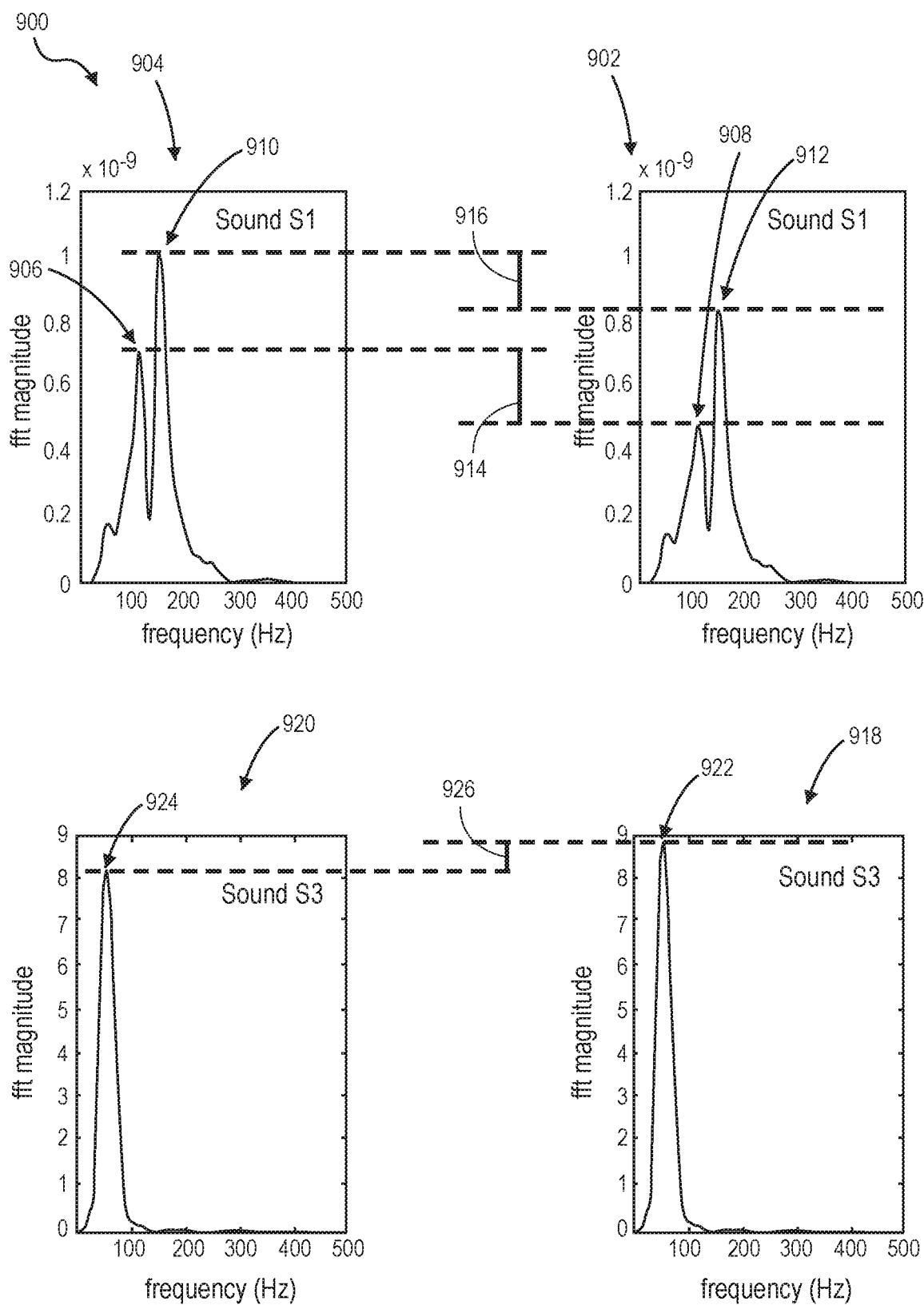

In some embodiments, the modification of a capture of a heart sound may include determining whether the capture of the heart sound to be modified and the capture of the heart sound being utilized for determining the amount of attenuation are expected to be negatively correlated. FIG. 9 illustrates an example of performance of a modification of a capture of a heart sound that is negatively correlated, according to embodiments herein.

Determining whether a heart sound being modified and a heart sound being utilized for determining the amount of attenuation are positively or negatively correlated may be based on the relationship between each of the heart sounds and the corresponding controls. For example, the heart sound being modified and the heart sound being utilized for determining the amount of attenuation may be determined to be positively correlated if both of the heart sounds are approximately (within 5%) equal to the corresponding controls or both of the heart sounds differ from the corresponding controls in the same direction and approximately (within 5%) a same amount. The heart sound being modified and the heart sound being utilized for determining the amount of attenuation may be determined to be negatively correlated if the heart sound being utilized for determining the amount of attenuation remains approximately (within 5%) equal to the corresponding control while the heart sound being modified varies from the corresponding control or the heart sound being utilized for determining the amount of attenuation varies from the corresponding control in one direction and the heart sound being modified varies from the corresponding control in the opposite direction.

In the illustrated embodiment, a capture 902 of an S1 heart sound is compared with a control 904 for the S1 heart sound to determine an amount of attenuation. In particular, a first peak 906 of the control 904 is compared with a first peak 908 of the capture 902. The comparison determines that the first peak 908 of the capture 902 is attenuated to be below the first peak 906 of the control 904, where a first amount of attenuation 914 of the capture 902 is determined based on the comparison. A second peak 910 of the control 904 is compared with a second peak 912 of the capture 902. The comparison determines that the second peak 912 of the capture is attenuated to be below the second peak 910 of the control 904, where a second amount of attenuation 916 of the capture 902 is determined based on the comparison.

Further, a capture 918 of an S3 heart sound is compared with a control 920 for the S3 heart sound. The comparison determines that a peak 922 of the capture 918 has increased as compared to a peak 924 of the control 920. In particular, the peak 922 of the capture 918 may have an increase 926 over the peak 924 of the control 920. Accordingly, it can be determined that the capture 918 of the S3 heart sound (i.e., the capture to be modified) has changed from the control 920 by being increased while the capture 902 of the S1 heart sound (i.e., the capture being utilized for determining the amount of attenuation) has changed from the control 904 by being decreased, thereby the capture 902 changing in the opposite direction as compared to the direction of change of the capture 918. Accordingly, the capture 918 of the S3 heart sound and the capture 902 of the S1 heart sound are determined to be negatively correlated in the illustrated instance.

In instances where the capture to be modified and the capture being utilized for determining the amount of attenuation are determined to be negatively correlated, the changes in the capture to be modified may be determined to be due to change in coupling and the capture to be modified may be modified to eliminate coupling effects. In some instances where the capture to be modified and the capture being utilized for determining the amount of attenuation are determined not to be negatively correlated, the changes in the capture to be modified may be determined to be due to changes in the capture to be modified separate rather than changes due to coupling.

Figure 10:
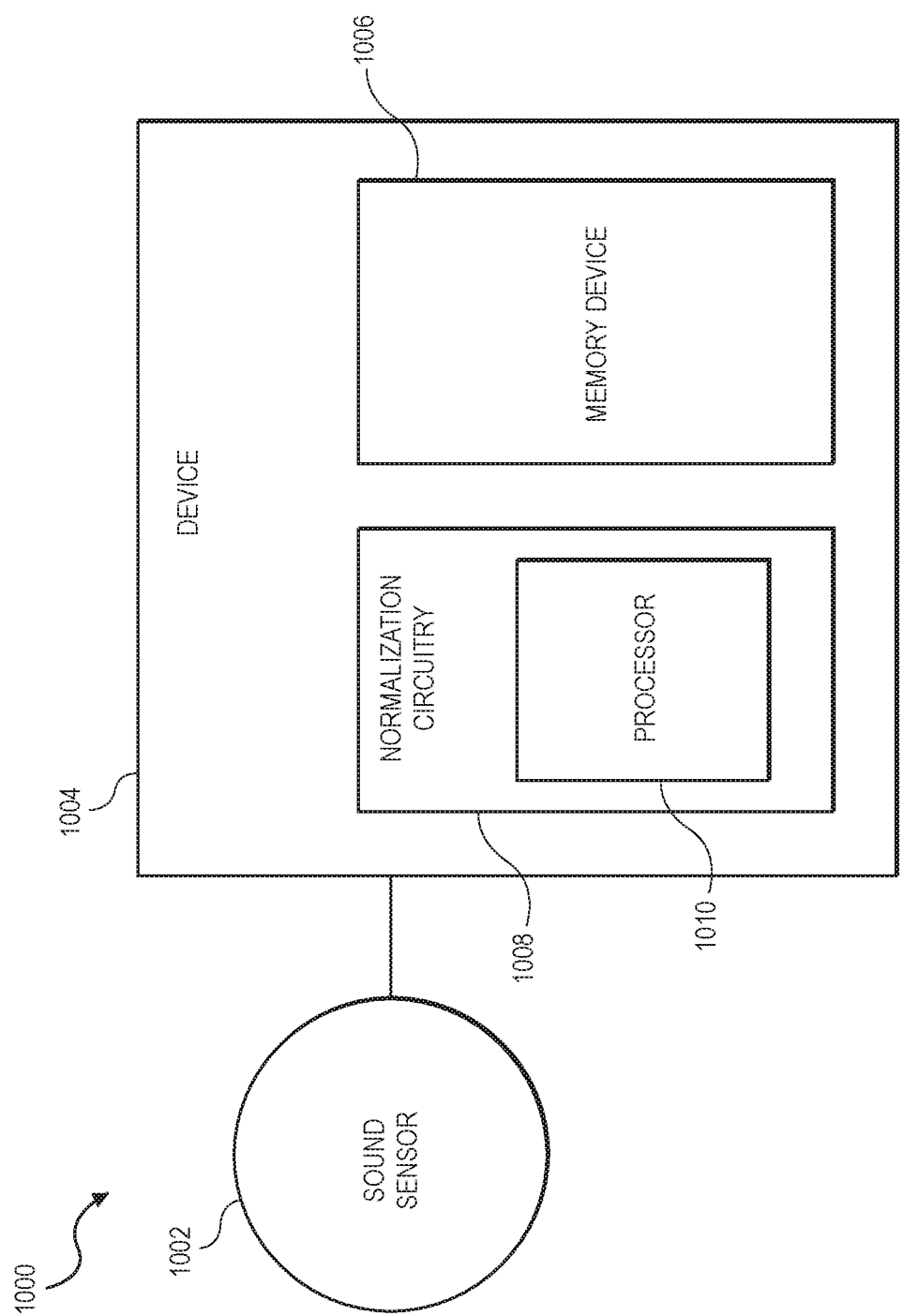
FIG. 10 illustrates an example system that may implement the procedure of FIG. 1, according to embodiments herein.

FIG. 10 illustrates an example system 1000 that may implement the procedure 100 of FIG. 1, according to embodiments herein. For example, the system 1000 may capture heart sounds and normalize the captured heart sounds via the procedure 100.

The system 1000 may include one or more sound sensors 1002. The sound sensors 1002 may be placed on a subject and may capture heart sounds of the subject. In particular, the sound sensors 1002 may detect the heart sounds of the subject and generate an electrical signal that represents the detected heart sounds. In some embodiments, the sound sensors 1002 may comprise electronic stethoscope, a piezoelectric sensor, an accelerometer, a microphone, any other sensor that can detect sounds and/or vibrations and generate an electrical signal that represents the detected sounds and/or vibrations, or some combination thereof.

The system 1000 may further include a device 1004. The device 1004 may be coupled to the sound sensors 1002 and may receive the captured heart sounds from the sound sensors 1002.

The device 1004 may include a memory device 1006 in which the captured heart sounds may be stored after being received and for processing. In some embodiments, the memory device 1006 may further include one or more instructions that, when executed by the device 1004, cause the device to perform the operations described herein. In other embodiments, the system 1000 may include one or more other computer-readable media with the instructions stored thereon.

The device 1004 may further include normalization circuitry 1008. The normalization circuitry 1008 may include a processor 1010. The normalization circuitry 1008 may perform the procedure 100 to normalize the captured heart sounds received from the sound sensors 1002. In particular, the normalization circuitry 1008 may retrieve the captured heart sounds from the memory device 1006 and normalize the heart sounds for further processing. In some embodiments, the normalization circuitry 1008 may generate a control (such as the control 704 (FIG. 7)) from one or more of the captured heart sounds and store the control in the memory device 1006 to be utilized for normalization of the captured heart sound. The one or more captured heart sounds utilized for generating the control may have been captured during an initialization cycle of the system 1000. The normalization circuitry 1008 may retrieve the control from the memory device 1006 to utilize for normalization of heart sounds.

The device 1004 may perform further processing of the normalized heart sounds. In other embodiments, the device 1004 may be coupled to another device (such as a server) and may provide the normalized heart sounds to the other device. The other device may perform further processing with the heart sounds.

While the system 1000 includes the sound sensors 1002 coupled to the device 1004 in the illustrated embodiment, it should be understood that the illustrated embodiment is an example embodiment and other embodiments may have other arrangements and/or additional elements. For example, the sound sensors 1002 may be implemented within the device 1004 in other embodiments.

While the captured heart sounds are disclosed as being stored on the memory device 1006 of the system 1000 in the illustrated embodiment, the captured heart sounds may be stored on one or more separate elements in other embodiments. For example, the captured heart sounds may be stored on a separate computing device or on one or more servers (such as the cloud) in other embodiments. The normalization circuitry 1008 may retrieve the captured heart sounds from the one or more separate elements and perform the normalization on the retrieved heart sounds. In some embodiments, the device 1004 may comprise a computing device or one or more servers (such as the cloud) located remote to the sound sensors 1002 and may receive the captured heart sounds via a network for communication between another device coupled to the sound sensors 1002 and the device 1004.

Figure 11:
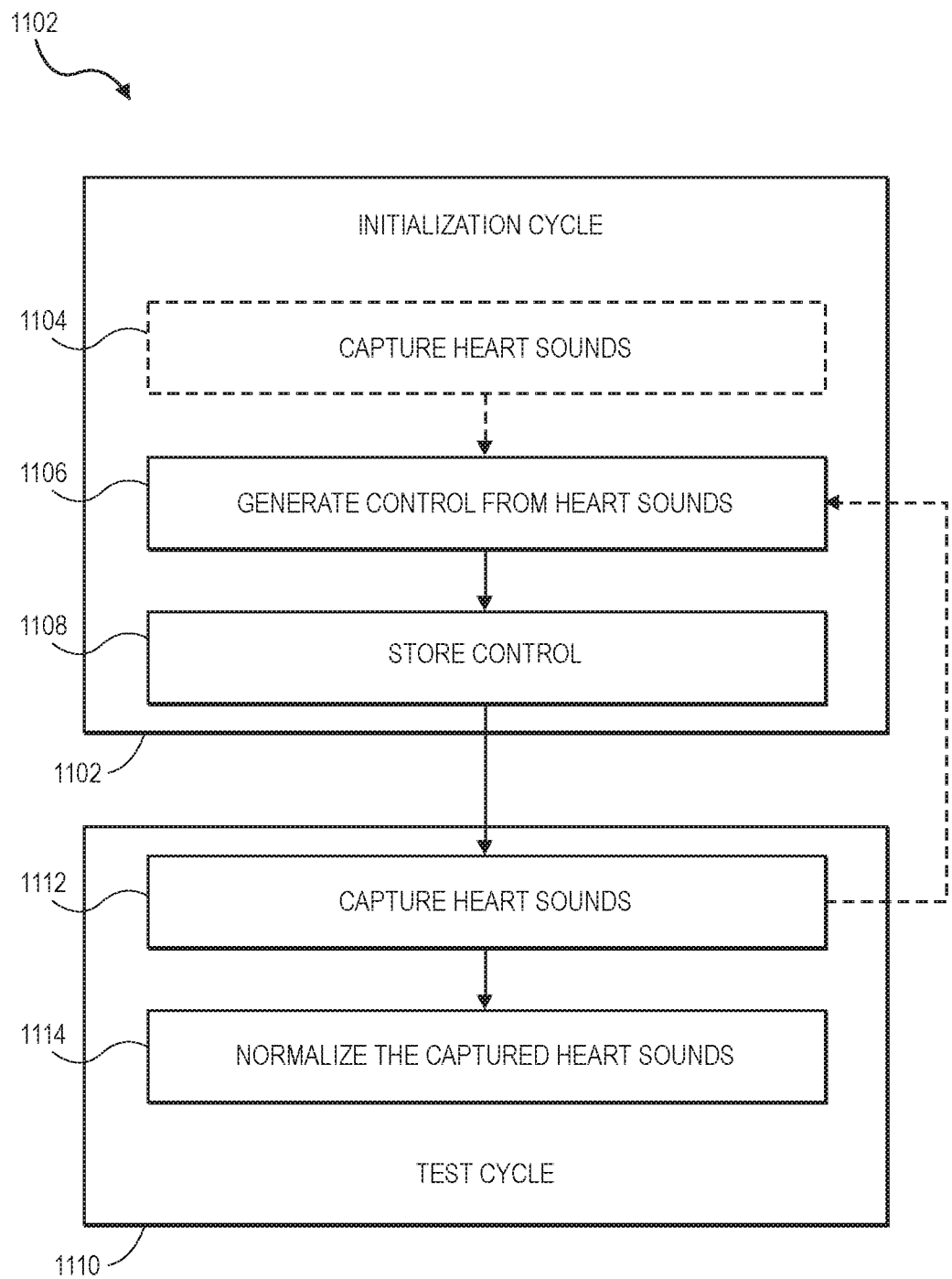
FIG. 11 illustrates an example procedure for initialization and normalization by a heart sound capture system, according to embodiments herein.

FIG. 11 illustrates an example procedure 1100 for initialization and normalization by a heart sound capture system, according to embodiments herein. For example, the procedure 1100 may be performed by the system 1000.

The procedure 1100 may initiate in an initialization cycle 1102. The initialization cycle 1102 may be performed in the presence of a care provider (such as a physician) to ensure that sound sensors of the system are properly placed on a subject during the initialization cycle 1102. In some embodiments, the system implementing the procedure 1100 may require an authorization of a user as a care provider to enter the initialization cycle 1102, such as embodiments where a control is generated from heart sounds captured in the initialization cycle 1102.

The initialization cycle 1102 may initiate by capturing one or more heart sounds in 1104. For example, one or more sound sensors (such as the sound sensors 1002 (FIG. 10)) may capture heart sounds of the subject and a device (such as the device 1004 (FIG. 10)) may store the captured heart sounds. In some embodiments, the capturing of the one or more heart sounds in 1104 may be omitted. In these embodiments, the procedure 1100 may initiate with 1112.

In 1106, a control may be generated from the one or more heart sounds captured in 1104. In some embodiments, a single heart sound from the one or more heart sounds may be stored as the control. In other embodiments, some portion of the one or more heart sounds may be averaged to produce a representation of a heart sound that may be stored as the control. In 1108, the control may be stored in a memory device (such as the memory device 1006 (FIG. 10)).

The procedure 1100 may proceed with a test cycle 1110. The test cycle 1110 may initiate by capturing one or more heart sounds in 1112. For example, one or more sound sensors may capture heart sounds of the subject and the device may store the captured heart sounds for analysis. In some embodiments, the one or more of the heart sounds captured in 1112 may be utilized in 1106 to generate the control.

In 1114, the heart sounds captured in 1112 may be normalized. In particular, the heart sounds may be normalized by implementing the procedure 100 (FIG. 1) for the heart sounds. The control produced in 1106 may be utilized for the normalization of the heart sounds. The normalized heart sounds may be stored for further processing.

EXAMPLE IMPLEMENTATIONS

The following examples are provided by way of illustration.

Example 1 may include one or more computer-readable media having instructions stored thereon, wherein the instructions, in response to execution by a device, cause the device to determine an amount of attenuation between a capture of a first heart sound and a control for the first heart sound, the capture of the first heart sound captured during a test cycle, modify a first portion of a capture of a second heart sound by a first amount, wherein the capture of the second heart sound is captured during the test cycle, wherein the first portion corresponds to a first frequency range, and wherein the first amount is determined based on the amount of attenuation, and modify a second portion of the capture of the second heart sound by a second amount, wherein the second portion corresponds to a second frequency range, and wherein the second amount is determined based on the amount of the attenuation.

Example 2 may include the one or more computer-readable media of example 1, wherein the instructions, in response to execution by the device, further cause the device to convert the capture of the first heart sound to a frequency-domain representation of the capture of the first heart sound, and comparing the frequency-domain representation of the capture of the first heart sound with the control of the first heart sound to determine the amount of attenuation.

Example 3 may include the one or more computer-readable media of example 1, wherein the instructions, in response to execution by the device, further cause the device to convert the capture of the second heart sound to a frequency-domain representation of the capture of the second heart sound, wherein to modify the first portion of the capture of the second heart sound includes to identify a first portion of the frequency-domain representation of the capture of the second heart sound, wherein the first portion corresponds to the first frequency range, and modify the first portion of the frequency-domain representation of the capture of the second heart sound by the first amount, and to modify the second portion of the capture of the second heart sound includes to identify a second portion of the capture of the frequency-domain representation of the capture of the second heart sound, wherein the second portion corresponds to the second frequency range, and modify the second portion of the frequency-domain representation of the capture of the second heart sound by the second amount, and the instructions, in response to execution by the device, further cause the device to convert the frequency-domain representation of the capture of the second heart sound to a time-domain representation of the capture of the second heart sound.

Example 4 may include the one or more computer-readable media of example 1, wherein to determine the amount of attenuation includes to determine an amount of attenuation of the capture of the first heart sound corresponding to the first frequency range, wherein the first amount is determined based on the attenuation of the capture of the first heart sound corresponding to the first frequency range, and determine an amount of attenuation of the capture of the first heart sound corresponding to the second frequency range, wherein the second amount is determined based on the attenuation of the capture of the first heart sound corresponding the second frequency range.

Example 5 may include the one or more computer-readable media of example 1, wherein the instructions, in response to execution by the device, further causes the device to receive an indication to utilize an S1 heart sound or an S2 heart sound as the first heart sound, wherein the first heart sound is either the S1 heart sound or the S2 heart sound based on the indication.

Example 6 may include the one or more computer-readable media of example 1, wherein the capture of the first heart sound is a first capture of the first heart sound, wherein the instructions, in response to execution by the device, further causes the device to capture a second capture of the first heart sound during an initialization cycle, and wherein the initialization cycle occurs prior to the test cycle, and store the second capture of the first heart sound as the control for the first heart sound.

Example 7 may include the one or more computer-readable media of example 1, wherein the instructions, in response to execution by the device, further causes the device to capture a plurality of captures of the first heart sound during a plurality of test cycles, wherein the plurality of test cycles occurs prior to the test cycle, generate an averaged representation of the first heart sound by averaging the plurality of captures of the first heart sound, and store the averaged representation of the first heart sound as the control of the first heart sound.

Example 8 may include the one or more computer-readable media of example 1, wherein the capture of the first heart sound is captured within a cardiac cycle, and wherein the capture of the second heart sound is captured within the cardiac cycle.

Example 9 may include a system for capturing heart sounds of a subject, comprising one or more sound sensors to sense heart sounds of the subject, and generate an electrical representation of the heart sounds, and one or more processors to identify a capture of a first heart sound from the electrical representation, compare the capture of the first heart sound with a control for the first heart sound to determine an amount of attenuation between the capture of the first heart sound and the control for the first heart sound, determine a first amount of modification and a second amount of modification based on the amount of attenuation, identify a capture of a second heart sound from the electrical representation, modify a first portion of the capture of the second heart sound by the first amount of modification, wherein the first portion of the capture corresponds to a first frequency range, and modification a second portion of the capture of the second heart sound by the second amount of modification, wherein the second portion of the capture corresponds to a second frequency range.

Example 10 may include the system of example 9, wherein to identify the capture of the first heart sound includes to identify a cardiac cycle from the electrical representation, and identify the capture of the first heart sound within the cardiac cycle, and identify the capture of the second heart sound includes to identify the capture of the second heart sound within the cardiac cycle.

Example 11 may include the system of example 9, wherein to compare the capture of the first heart sound with the control includes to convert the capture of the first heart sound to a frequency-domain representation of the capture of the first heart sound, and compare the frequency-domain representation of the capture of the first heart sound with the control of the first heart sound.

Example 12 may include the system of example 9, wherein to determine the first amount of modification and the second amount of modification includes to utilize the amount of attenuation in a frequency-dependent equation to determine the first amount of modification and the second amount of modification, wherein the first amount of modification and the second amount of modification are different based on the first amount of modification being for the first frequency range and the second amount of modification being for the second frequency range.

Example 13 may include the system of example 9, wherein the one or more processors are further to convert the capture of the second heart sound to a frequency-domain representation of the capture of the second heart sound, to modify the first portion of the capture of the second heart sound includes to identify a first portion of the frequency-domain representation, wherein the first portion of the frequency-domain representation corresponds to the first frequency range, and modify the first portion of the frequency-domain representation by the first amount of modification, to modify the second portion of the capture of the second heart sound includes to identify a second portion of the frequency-domain representation, wherein the second portion of the frequency-domain representation corresponds to the second frequency range, and modify the second portion of the frequency-domain representation by the second amount of modification, and the one or more processors are further to convert the frequency-domain representation to a time-domain representation of the capture of the second heart sound.

Example 14 may include the system of example 9, wherein the heart sounds of the subject are first heart sounds of the subject, the capture of the first heart sound is a first capture of the first heart sound, the one or more sound sensors are to sense second heart sounds of the subject during an initialization cycle, generate an electrical representation of the second heart sounds, and the one or more processors are to identify a second capture of the first heart sound from the electrical representation of the second heart sounds, and store the second capture of the first heart sound as the control for the first heart sound.

Example 15 may include the system of example 9, wherein the one or more processors are further to receive an indication to utilize an S1 heart sound or an S2 heart sound as the first heart sound, wherein to identify the capture of the first heart sound comprises to identify a capture of the S1 heart sound or the S2 heart sound from the electrical representation based on the indication.

Example 16 may include a method of normalizing heart sounds, comprising comparing a capture of a first heart sound of a test cycle with a control for the first heart sound, determining an amount of attenuation between the capture of the first heart sound and the control for the first heart sound based on the comparison of the capture of the first heart sound and the control for the first heart sound, modifying a first portion of a capture of a second heart sound of the test cycle by a first amount, wherein the first portion corresponds to a first frequency range, and wherein the first amount is determined based on the amount of attenuation, and modifying a second portion of the capture of the second heart sound of the test cycle by a second amount, wherein the second portion corresponds to a second frequency range, and wherein the second amount is determined based on the amount of attenuation.

Example 17 may include the method of example 16, further comprising converting the capture of the second heart sound to a frequency-domain representation of the capture of the second heart sound, wherein modifying the first portion of the capture of the second heart sound includes identifying a first portion of the frequency-domain representation of the capture of the second heart sound, wherein the first portion corresponds to the first frequency range, and modifying the first portion of the frequency-domain representation of the capture of the second heart sound by the first amount, and modifying the second portion of the capture of the second heart sound includes identifying a second portion of the capture of the frequency-domain representation of the capture of the second heart sound, wherein the second portion corresponds to the second frequency range, and modifying the second portion of the frequency-domain representation of the capture of the second heart sound by the second amount, and the method further comprises converting the frequency-domain representation of the capture of the second heart sound to a time-domain representation of the capture of the second heart sound.

Example 18 may include the method of example 16, wherein determining the amount of attenuation includes determining an amount of attenuation between the capture of the first heart sound and the control for the first heart sound corresponding to the first frequency range, wherein the first amount is determined based on the attenuation between the capture of the first heart sound and the control of the first heart sound corresponding to the first frequency range, and determining an amount of attenuation between the capture of the first heart sound and the control of the first heart sound corresponding to the second frequency range, wherein the second amount is determined based on the attenuation between the capture of the first heart sound and the control of the first heart sound corresponding to the second frequency range.

Example 19 may include the method of example 16, wherein the capture of the first heart sound is a first capture of the first heart sound, wherein the method further comprises capturing a second capture of the first heart sound during an initialization cycle and storing the second capture as the control, and wherein the initialization cycle occurs prior to the test cycle.

Example 20 may include the method of example 16, further comprising capturing a plurality of captures of the first heart sound during a plurality of test cycles, wherein the plurality of test cycles occurs prior to the test cycle, and generating an averaged representation of the first heart sound by averaging the plurality of captures of the first heart sound, wherein the control of the first heart sound is the averaged representation of the first heart sound.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present specification.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

In some cases, the teachings of the present specification may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof. In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe. Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

What is claimed is:

1. One or more computer-readable media having instructions stored thereon, wherein the instructions, in response to execution by a device, cause the device to:

determine an amount of attenuation between a capture of a first heart sound and a control for the first heart sound, the capture of the first heart sound captured during a test cycle;

modify a first portion of a capture of a second heart sound by a first amount, wherein the capture of the second heart sound is captured during the test cycle, wherein the first portion corresponds to a first frequency range, and wherein the first amount is determined based on the amount of attenuation; and modify a second portion of the capture of the second heart sound by a second amount, wherein the second portion corresponds to a second frequency range, and wherein the second amount is determined based on the amount of the attenuation;

wherein the capture of the first heart sound is a first capture of the first heart sound, wherein the instructions, in response to execution by the device, further causes the device to:

capture a second capture of the first heart sound during an initialization cycle, and wherein the initialization cycle occurs prior to the test cycle; and store the second capture of the first heart sound as the control for the first heart sound.

2. The one or more computer-readable media of claim 1, wherein the instructions, in response to execution by the device, further cause the device to:

convert the capture of the first heart sound to a frequency-domain representation of the capture of the first heart sound; and compare the frequency-domain representation of the capture of the first heart sound with the control of the first heart sound to determine the amount of attenuation.

3. The one or more computer-readable media of claim 1, wherein the instructions, in response to execution by the device, further cause the device to convert the capture of the second heart sound to a frequency-domain representation of the capture of the second heart sound, wherein:

to modify the first portion of the capture of the second heart sound includes to:

identify a first portion of the frequency-domain representation of the capture of the second heart sound, wherein the first portion corresponds to the first frequency range; and modify the first portion of the frequency-domain representation of the capture of the second heart sound by the first amount; and to modify the second portion of the capture of the second heart sound includes to:

identify a second portion of the capture of the frequency-domain representation of the capture of the second heart sound, wherein the second portion corresponds to the second frequency range; and modify the second portion of the frequency-domain representation of the capture of the second heart sound by the second amount; and the instructions, in response to execution by the device, further cause the device to convert the frequency-domain representation of the capture of the second heart sound to a time-domain representation of the capture of the second heart sound.

4. The one or more computer-readable media of claim 1, wherein to determine the amount of attenuation includes to:

determine an amount of attenuation of the capture of the first heart sound corresponding to the first frequency range, wherein the first amount is determined based on the attenuation of the capture of the first heart sound corresponding to the first frequency range; and determine an amount of attenuation of the capture of the first heart sound corresponding to the second frequency range, wherein the second amount is determined based on the attenuation of the capture of the first heart sound corresponding the second frequency range.

5. The one or more computer-readable media of claim 1, wherein the instructions, in response to execution by the device, further causes the device to receive an indication to utilize an S1 heart sound or an S2 heart sound as the first heart sound, wherein the first heart sound is either the S1 heart sound or the S2 heart sound based on the indication.

6. The one or more computer-readable media of claim 1, wherein the instructions, in response to execution by the device, further causes the device to:
   capture a plurality of captures of the first heart sound during a plurality of test cycles, wherein the plurality of test cycles occurs prior to the test cycle;
   generate an averaged representation of the first heart sound by averaging the plurality of captures of the first heart sound; and
   store the averaged representation of the first heart sound as the control of the first heart sound.

7. The one or more computer-readable media of claim 1, wherein the capture of the first heart sound is captured within a cardiac cycle, and wherein the capture of the second heart sound is captured within the cardiac cycle.

8. A system for capturing heart sounds of a subject, comprising:
   one or more sound sensors to:
      sense heart sounds of the subject; and
      generate an electrical representation of the heart sounds; and
   one or more processors to:
      identify a capture of a first heart sound from the electrical representation, wherein the capture of the first heart sound occurs during a test cycle;
      compare the capture of the first heart sound with a control for the first heart sound to determine an amount of attenuation between the capture of the first heart sound and the control for the first heart sound;
      determine a first amount of modification and a second amount of modification based on the amount of attenuation;
      identify a capture of a second heart sound from the electrical representation;
      modify a first portion of the capture of the second heart sound by the first amount of modification, wherein the first portion of the capture corresponds to a first frequency range;
      modify a second portion of the capture of the second heart sound by the second amount of modification, wherein the second portion of the capture corresponds to a second frequency range;
      capture a plurality of captures of the first heart sound during a plurality of test cycles, wherein the plurality of test cycles occurs prior to the test cycle;
      generate an averaged representation of the first heart sound by averaging the plurality of captures of the first heart sound; and
      store the averaged representation of the first heart sound as the control of the first heart sound.

9. The system of claim 8, wherein to:
   identify the capture of the first heart sound includes to:
      identify a cardiac cycle from the electrical representation; and
      identify the capture of the first heart sound within the cardiac cycle; and
   identify the capture of the second heart sound includes to:
      identify the capture of the second heart sound within the cardiac cycle.

10. The system of claim 8, wherein to compare the capture of the first heart sound with the control includes to:
    convert the capture of the first heart sound to a frequency-domain representation of the capture of the first heart sound; and
    compare the frequency-domain representation of the capture of the first heart sound with the control of the first heart sound.

11. The system of claim 8, wherein to determine the first amount of modification and the second amount of modification includes to utilize the amount of attenuation in a frequency-dependent equation to determine the first amount of modification and the second amount of modification, wherein the first amount of modification and the second amount of modification are different based on the first amount of modification being for the first frequency range and the second amount of modification being for the second frequency range.

12. The system of claim 8, wherein:
    the one or more processors are further to convert the capture of the second heart sound to a frequency-domain representation of the capture of the second heart sound;
    to modify the first portion of the capture of the second heart sound includes to:
       identify a first portion of the frequency-domain representation, wherein the first portion of the frequency-domain representation corresponds to the first frequency range; and
       modify the first portion of the frequency-domain representation by the first amount of modification;
    to modify the second portion of the capture of the second heart sound includes to:
       identify a second portion of the frequency-domain representation, wherein the second portion of the frequency-domain representation corresponds to the second frequency range; and
       modify the second portion of the frequency-domain representation by the second amount of modification; and
    the one or more processors are further to convert the frequency-domain representation to a time-domain representation of the capture of the second heart sound.

13. The system of claim 8, wherein:
    the heart sounds of the subject are first heart sounds of the subject;
    the capture of the first heart sound is a first capture of the first heart sound;
    the one or more sound sensors are to:
       sense second heart sounds of the subject during an initialization cycle;
       generate an electrical representation of the second heart sounds; and
    the one or more processors are to:
       identify a second capture of the first heart sound from the electrical representation of the second heart sounds; and
       store the second capture of the first heart sound as the control for the first heart sound.

14. The system of claim 8, wherein the one or more processors are further to receive an indication to utilize an S1 heart sound or an S2 heart sound as the first heart sound, wherein to identify the capture of the first heart sound comprises to identify a capture of an S1 heart sound or an S2 heart sound from the electrical representation based on the indication.

15. A method of normalizing heart sounds, comprising:
comparing a capture of a first heart sound of a test cycle with a control for the first heart sound;
determining an amount of attenuation of the capture of the first heart sound based on the comparison of the capture of the first heart sound and the control for the first heart sound;
modifying a first portion of a capture of a second heart sound of the test cycle by a first amount, wherein the first portion corresponds to a first frequency range, and wherein the first amount is determined based on the amount of attenuation; and
modifying a second portion of the capture of the second heart sound of the test cycle by a second amount, wherein the second portion corresponds to a second frequency range, and wherein the second amount is determined based on the amount of attenuation;
wherein the capture of the first heart sound is a first capture of the first heart sound, wherein the method further comprises capturing a second capture of the first heart sound during an initialization cycle and storing the second capture as the control, and wherein the initialization cycle occurs prior to the test cycle.

16. The method of claim 15, further comprising converting the capture of the second heart sound to a frequency-domain representation of the capture of the second heart sound, wherein:
modifying the first portion of the capture of the second heart sound includes:
identifying a first portion of the frequency-domain representation of the capture of the second heart sound, wherein the first portion corresponds to the first frequency range; and
modifying the first portion of the frequency-domain representation of the capture of the second heart sound by the first amount; and
modifying the second portion of the capture of the second heart sound includes:
identifying a second portion of the capture of the frequency-domain representation of the capture of the second heart sound, wherein the second portion corresponds to the second frequency range; and
modifying the second portion of the frequency-domain representation of the capture of the second heart sound by the second amount; and
the method further comprises converting the frequency-domain representation of the capture of the second heart sound to a time-domain representation of the capture of the second heart sound.

17. The method of claim 15, wherein determining the amount of attenuation includes:
determining an amount of attenuation between the capture of the first heart sound and the control for the first heart sound corresponding to the first frequency range, wherein the first amount is determined based on the attenuation between the capture of the first heart sound and the control for the first heart sound corresponding to the first frequency range; and
determining an amount of attenuation between the capture of the first heart sound and the control for the first heart sound corresponding to the second frequency range, wherein the second amount is determined based on the attenuation between the capture of the first heart sound and the control for the first heart sound corresponding to the second frequency range.

18. The method of claim 15, further comprising:
capturing a plurality of captures of the first heart sound during a plurality of test cycles, wherein the plurality of test cycles occurs prior to the test cycle; and
generating an averaged representation of the first heart sound by averaging the plurality of captures of the first heart sound, wherein the control of the first heart sound is the averaged representation of the first heart sound.

* * * * *